(12) United States Patent
Bourdon (10) Patent No.: US 9,353,194 B2
(45) Date of Patent: May 31, 2016

(54) PROCESS FOR PREPARING A CROSSLINKED HYALURONIC ACID GEL VIA HOMOGENIZATION IN A DEFORMABLE POUCH

(75) Inventor: Francois Bourdon, Gaillard (FR)

(73) Assignee: TEOXANE, Geneva (CH)

( * ) Notice: Subject to any disclaimer, the term of this patent is extended or adjusted under 35 U.S.C. 154(b) by 0 days.

(21) Appl. No.: 13/266,638

(22) PCT Filed: May 7, 2010

(86) PCT No.: PCT/IB2010/052027
§ 371 (c)(1),
(2), (4) Date: Dec. 15, 2011

(87) PCT Pub. No.: WO2010/131175
PCT Pub. Date: Nov. 18, 2010

(65) Prior Publication Data
US 2012/0108537 A1    May 3, 2012

(30) Foreign Application Priority Data
May 11, 2009 (FR) ...................................... 09 53108

(51) Int. Cl.
| | | |
|---|---|---|
| C08B 37/08 | (2006.01) | |
| A61K 8/04 | (2006.01) | |
| A61K 8/73 | (2006.01) | |
| A61Q 19/08 | (2006.01) | |
| C08J 3/075 | (2006.01) | |
| C08J 3/24 | (2006.01) | |

(52) U.S. Cl.
CPC ............. *C08B 37/0072* (2013.01); *A61K 8/042* (2013.01); *A61K 8/735* (2013.01); *A61Q 19/08* (2013.01); *C08J 3/075* (2013.01); *C08J 3/24* (2013.01); *C08J 2305/08* (2013.01)

(58) Field of Classification Search
None
See application file for complete search history.

(56) References Cited

U.S. PATENT DOCUMENTS

| | | | | |
|---|---|---|---|---|
| 4,716,154 A | * | 12/1987 | Malson et al. | .................. 514/54 |
| 2003/0148995 A1 | | 8/2003 | Piron et al. | |
| 2005/0142152 A1 | | 6/2005 | Leshchiner et al. | |
| 2005/0281880 A1 | * | 12/2005 | Wang | ............................ 424/486 |
| 2006/0105022 A1 | | 5/2006 | Yokokawa et al. | |
| 2007/0036745 A1 | | 2/2007 | Leshchiner et al. | |
| 2008/0139796 A1 | | 6/2008 | Yagi et al. | |
| 2013/0237615 A1 | * | 9/2013 | Meunier et al. | ................ 514/777 |

FOREIGN PATENT DOCUMENTS

| | | | | |
|---|---|---|---|---|
| EP | 1818344 A1 | * | 8/2007 | ............. C08B 37/08 |
| WO | WO 96/26681 A1 | | 9/1996 | |
| WO | WO 2005/112888 A2 | | 12/2005 | |
| WO | WO 2006/056204 A1 | | 6/2006 | |

OTHER PUBLICATIONS

Lee, B., Homemade Slime, Nov. 4, 1997. http://www.madsci.org/experiments/archive/878680114.Ch.html.*
LAT, Mar. 12, 2010, response to inquiry, "Any DIY Hyaluronic Acid Serum recipies?" on http://www.essentialdayspa.com/forum/viewthread.php?tid=31997.*
International Search Report dated Sep. 3, 2010 in International Application No. PCT/IB2010/052027.
Written Opinion of the International Searching Authority dated Sep. 3, 2010 in International Application No. PCT/IB2010/052027.

* cited by examiner

*Primary Examiner* — Eric Olson
*Assistant Examiner* — Dale R Miller
(74) *Attorney, Agent, or Firm* — Shumaker, Loop & Kendrick, LLP (57) ABSTRACT

A process for preparing a crosslinked gel of at least one polymer or one of its salts, including a) providing an aqueous medium containing at least one polymer, b) forming a homogenous gel from the medium from step a), c) bringing the gel obtained in step b) into contact with an effective amount of at least one crosslinking agent; d) crosslinking the mixture formed in step c); and e) recovering the crosslinked hydrogel, wherein at least steps a) to d) are carried out within a hermetic cavity delimited at least partially by a deformable wall, the mixture present in the cavity being exposed, in step d), to conditions conducive to crosslinking.

17 Claims, 7 Drawing Sheets

PROCESS FOR PREPARING A CROSSLINKED HYALURONIC ACID GEL VIA HOMOGENIZATION IN A DEFORMABLE POUCH

BACKGROUND

The present disclosure relates to a novel method of preparing hydrogels based on a crosslinked polymer, more particularly that are derived from polysaccharide, and preferably from hyaluronic acid or from one of its salts.

In particular, disclosed is a process that makes it possible to obtain a hydrogel quality that is particularly advantageous for the long-lasting filling of volume defects of the skin.

Hyaluronic acid is known for its viscoelastic properties and also its very great propensity to absorb water. Its properties largely explain the elasticity of the skin. Its biocompatibilities, tolerance and lack of toxicity are such that for more than ten years, this molecule has had applications in medical and cosmetic fields.

Hyaluronic acid is especially used for filling wrinkles.

Wrinkles originate more particularly from a local weakening of the structure of the dermis. Thus, the injection into the dermis of a crosslinked polymer hydrogel at the wrinkles to be treated makes it possible to reduce, or even eliminate the depression of the epidermis. The injections are carried out using pre-filled syringes containing the sterile hydrogel. However, the deepest depressions require relatively viscous gels to be injected.

It is known, generally, that any molecule is much more resistant to degradation and to heat when it is crosslinked. Thus, the advantage of crosslinking hyaluronic acid is known. This crosslinked hyaluronic acid is, in addition, much more stable in the body than the hyaluronic acid molecule. It is also better able to withstand sterilization in an autoclave.

A certain number of processes for preparing crosslinked gels of polymers, or even of polysaccharides, has already been proposed. Generally, these processes require two main steps, the first consists in dissolving the polymer in question in a medium suitable for its homogenization and the second aims to add an agent capable of inducing the crosslinking thereof. Depending on the specific conditions used for the crosslinking, it proves possible to adjust the viscosity or else the rheological properties of the crosslinked hydrogel formed.

By way of illustration of these processes, mention may especially be made of the processes described in US 2006/0105022, which comprises the use of a mixture comprising at least 10% of hyaluronic acid, a crosslinking agent and water under acid or basic conditions, in WO 2006/056204, which comprises a step of treating the hyaluronic acid gel crosslinked with divinyl sulphone and in US 2007/0036745, which results in a cohesive gel starting from a hyaluronan polymer crosslinked with divinyl sulphone (DVS).

However, all of these processes do not give complete satisfaction.

As it emerges from the aforegoing, the crosslinking makes it necessary to first have a homogeneous solution of the starting polymer.

However, putting a polymer, like hyaluronic acid, into solution by dissolving needs to be carried out with gentle agitation, in order to preserve, as best possible, the integrity and the initial size of the polymer chains, of the order of several millions of Daltons in the case of hyaluronic acid. In order to satisfy this constraint, this homogenization step is conventionally carried out under very reduced mechanical agitation and therefore needs to be prolonged in time, for example up to 12 hours which, on an industrial scale, proves prejudicial.

As regards the crosslinking, which conditions the qualities of the final crosslinked hydrogel, it is also important that it be uniform in the gel.

However, the current processes do not make it possible to give a gel an identical degree of crosslinking at any point. Indeed, these processes generally require formulating the polymer within a receptacle, such as pots or tanks (batch) which does not allow a uniform diffusion of the environmental conditions necessary for the crosslinking to take place or the stopping thereof, especially in the case of a static crosslinking. This results in crosslinked gels which may have a relative disparity in terms of degree of crosslinking, this uniformity affecting of course their qualities.

Finally, with regard to the use for which these gels are intended, it is important to ensure that they have irreproachable sanitary qualities. This harmlessness could especially be reinforced by considerably minimizing the contacts of the various media acquired in these processes with the external environment.

SUMMARY

The present disclosure aims precisely to propose a process that makes it possible to respond favourably to the constraints mentioned above.

Thus, the inventors have discovered that it is possible not only to improve the homogenization of the polymer before crosslinking, but also to improve the correct progression of the crosslinking process, subject to using all of the steps necessary for its conversion to a crosslinked gel within a specific hermetic cavity.

Thus, the present disclosure relates, according to a first of its aspects, to a process for preparing a crosslinked gel of at least one polymer or one of its salts, comprising at least the steps that consist in:

a) providing an aqueous medium containing said polymer,
b) forming a homogenous gel from the medium from step a),
c) bringing the gel obtained in step b) into contact with an effective amount of at least one crosslinking agent;
d) crosslinking said mixture formed in step c); and
e) recovering said crosslinked hydrogel, wherein at least said steps a) to d) are carried out within a hermetic cavity delimited at least partially by a deformable wall, said mixture present in the cavity being exposed, in step d), to conditions conducive to crosslinking.

According to one particular embodiment, the process further comprises a step f) of stopping the crosslinking that consists in exposing the crosslinked gel to conditions conducive to stopping its crosslinking, this step possibly being carried out prior to, together with or subsequent to the recovery step e).

According to one preferred embodiment variant, step f) is carried out prior to the recovery step e).

According to this advantageous embodiment, all of steps a) to d) and f) are carried out within said cavity. The crosslinking is stopped by exposing the gel present in the hermetic cavity to conditions conducive to stopping the crosslinking.

According to one favoured embodiment, the receptacle in which the cavity is made may be provided with a sealing means, on the one hand conducive to the incorporation of reactants and, on the other hand, suitable for guaranteeing a total hermeticity during steps b) to d), or even a) and f).

However, this hermeticity may also be obtained via the adjustment of the receptacle within the apparatus used for ensuring the homogenization of step b).

According to one particular embodiment, step a) of said process is characterized by the fact that the cavity initially contains the polymer or one of its salts, said aqueous medium being introduced consecutively or vice versa.

According to one preferred embodiment variant, said cavity is made within a deformable pouch.

More particularly, the polymer is a polysaccharide, hyaluronic acid or one of its salts.

Advantageously, the polymer gel obtained is a single-phase gel and more particularly a solid gel, that is to say stripped of the ability to flow under its own weight, like, for example, a gum.

Against all expectation and as it emerges from the tests presented below, the fact of carrying out the homogenization and the crosslinking in a cavity as defined above, and more particularly a deformable pouch, makes it possible to obtain a hydrogel quality that cannot be obtained by means of a conventional process, that is to say in which all of the operations are carried out within an open and solid receptacle, that is to say a non-hermetic and non-deformable receptacle.

The deformability properties of the receptacle according to the invention and its hermetic nature make it possible, it appears, to carry out the homogenization and crosslinking steps under optimal conditions that result in a crosslinked gel being obtained that has injectability properties greater than those displayed by a gel obtained according to a conventional process. The injectability properties in question according to the invention are those displayed by the crosslinked gel, recovered once the crosslinking has stopped, that is to say without complementary treatment.

Thus, the process according to the invention makes possible an agitation according to step a) by deformation of the wall or of all of the deformable walls delimiting the cavity, or even of the receptacle when it is a pouch, containing said gel.

The advantages of this technique are characterized by a homogenization that is gentle, optimized, rapid and without risk of contamination of the product.

In this respect, it has to be noticed that the process of the invention is advantageously compatible with the implementation of polymers having a very high molecular weight, for example greater than 4 MDa, unlike the conventional methods of homogenization.

Indeed, conventional methods display a limitation with respect to the molecular weight of polymers in so far as the high viscosity exhibited by gels obtained from such polymers is not suitable for getting a satisfactory homogenization.

As regards the crosslinking reaction, it may also be carried out under optimal conditions, with respect, on the one hand, to the good homogeneity of the gel obtained at the end of step b) and, on the other hand, to the nature of the receptacle containing said gel. Advantageously, this hermetic receptacle may be directly exposed, in its entirety, to the conditions used for the crosslinking.

For example, in the case of a crosslinking by thermal means, the latter may advantageously be carried out by directly immersing the receptacle, for example the pouch, in a thermostatted bath at a temperature conducive to this crosslinking, that thus makes it possible to ensure an excellent heat conduction and a homogeneous temperature gradient over the entire volume of the gel.

The process according to the invention also proves particularly advantageous from the point of view of the harmlessness in so far as it effectively minimizes the contacts of the uncrosslinked, then crosslinked, gel with the atmosphere.

Finally, another substantial advantage from an industrial point of view of the process according to the invention lies in its compatibility with an implementation of the crosslinking step on a substantially larger amount of material than that which can be envisaged with the current processes.

DETAILED DESCRIPTION OF EMBODIMENTS

I) Receptacle

As specified above, the process according to the invention implements a hermetic receptacle in which a cavity delimited at least partially by a deformable wall is made.

Figure 1:
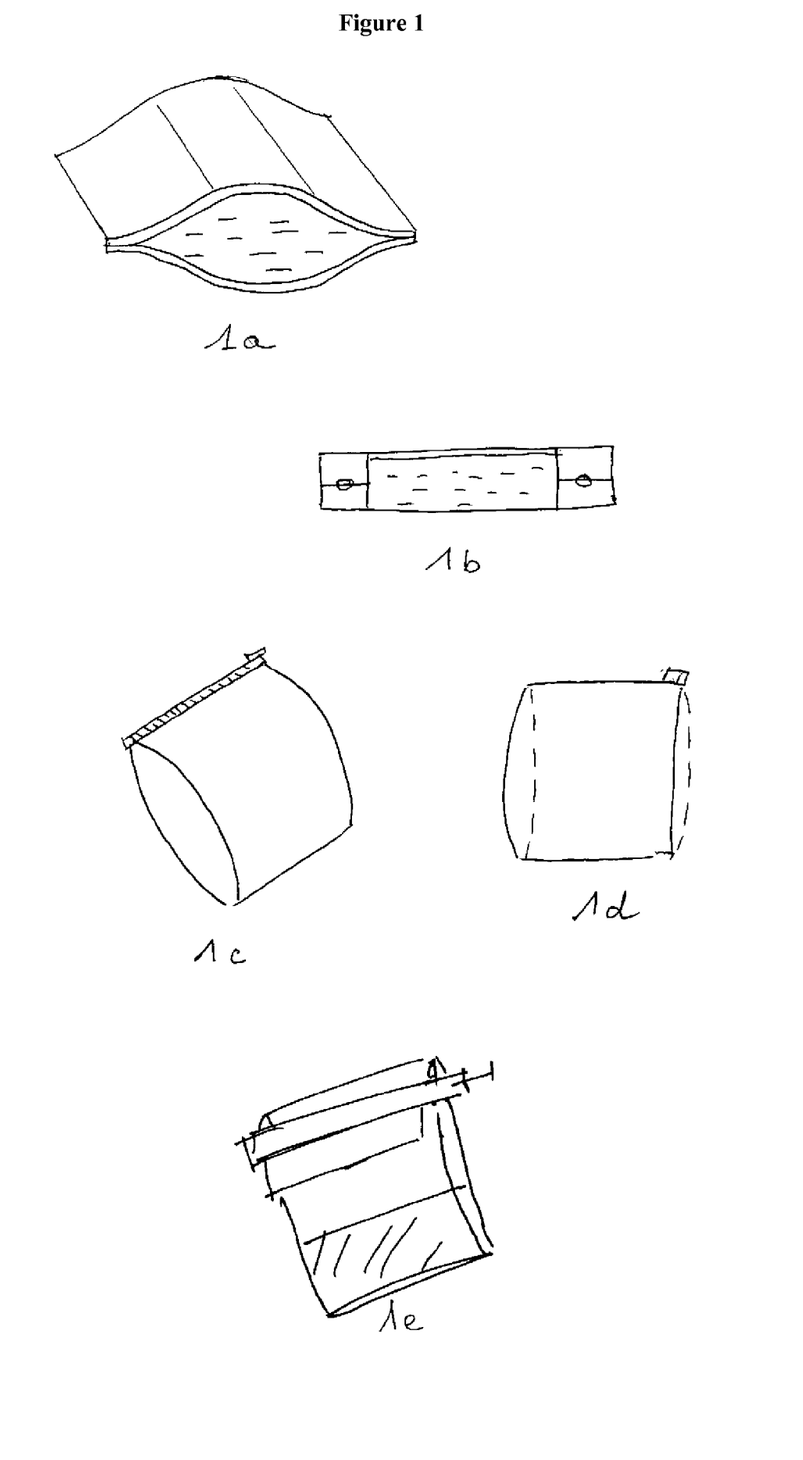
FIGS. 1*a* to 1*e*: illustrate schematic representations of receptacles in accordance with the invention.

In FIG. 1 below, various embodiments of such a receptacle are represented.

For example, FIG. 1b represents an embodiment provided with a single deformable wall positioned at the surface of a frame that makes a hermetic cavity.

Advantageously, all of the walls delimiting the cavity are deformable.

A pouch, like those illustrated in FIGS. 1a, 1c, 1d and 1e, is especially representative of this embodiment.

Firstly, the deformable wall, or even the pouch, has mechanical properties which are adjusted in order to withstand the stresses exerted, especially internally, during the homogenization, and during the handling of the receptacle, in order to prevent any risk of tearing.

As specified above, the deformable wall or the pouch has a degree of deformability such that it can be deformed manually, that is to say under the effect of a pressure resulting, for example, from a simple palpation.

As specified below, this pressure may also be applied mechanically.

The degree of deformability of the deformable wall may be such that, according to one particular embodiment, it allows the contact, especially when the cavity is empty, of the deformable wall with the face which is opposite it.

Furthermore, said wall, or even said pouch, being capable of being subjected to specific temperature conditions, especially with respect to the crosslinking step, exhibits properties of resistance to large temperature variations, for example from 0 to 140° C.

The receptacle, or even the pouch, according to one practical aspect but also with a view to limiting as much as possible the contacts with the outside environment, has a hermetic nature.

The receptacle according to the invention may however be advantageously equipped with an opening system or port, preferably resealable, and suitable for introducing any compound used for the manufacture of a gel in accordance with the invention.

Such opening systems are especially illustrated in FIGS. 1c and 1d.

This system may, for example, be suitable for introducing, via a needle for example, additional components within said cavity (FIG. 1d).

Thus, the cavity may initially contain the polymer and the aqueous medium is introduced subsequently there into via such an opening system.

An opening system or port similar to that described in document EP 0 812 158 may especially be envisaged.

According to another alternative, when the receptacle is a pouch, the closure system may be in the form of at least one tongue positioned at the upper edge of the pouch and over the entire length of the back of the latter, the side edges of said tongue possibly being folded over at the periphery (FIG. 1e).

According to yet another alternative, the closure system of said pouch is in the form of a zip, similar to those that can be found on certain food bags (FIG. 1c).

Advantageously, the constituent deformable membrane(s) of said receptacle has (have) a thickness between 10 μm and 1 mm, preferably between 40 μm and 0.3 mm.

The volume of said cavity is also suitable for the total amount of compounds used for the manufacture of a hydrogel in accordance with the invention.

According to one particular embodiment, the cavity has a volume such that said medium in question in step a) fills at least 1/10, preferably at least 1/5 thereof.

The cavity in question according to the invention preferably has a volume of the order of 50 to 10 000 $cm^3$, preferably of 200 to 4000 $cm^3$.

Said cavity may advantageously have a regular shape, for example square or rectangular or else be of small carton type, such as those presented in FIG. 1.

The receptacle in question according to the invention may advantageously lend itself to a storage of the medium that it contains under an inert atmosphere, or even under vacuum.

Advantageously, this receptacle is made from a material that is inert with respect to the various compounds used for the manufacture of a hydrogel in accordance with the invention.

The deformable wall or the pouch is, furthermore, made from a material which makes it possible to give satisfaction with respect to the mechanical characteristics described above. This material may especially be chosen from plastic polymers, like, in particular, pharmaceutical grade polyethylene for use in the pharmaceutical or biomedical industry.

With regard to the destination of the products resulting from a process according to the invention, the receptacle is advantageously sterile. In order to fulfil this requirement, the latter, before use, may also be packaged in a sterile packaging.

In order to facilitate the implementation of a process in accordance with the invention, at least one of the components of the receptacle is preferably transparent or is in a material that is clear enough to be able to observe the changes carried out internally.

As specified above, according to one preferred variant, the receptacle is a pouch.

One specific embodiment of this preferred variant may consist of a two-sided pouch having, preferably along one of its edges, a closure means of screw thread type onto which a cap may be screwed (FIG. 1d) or else a closure means of zip/slide type (FIG. 1c).

According to another particular embodiment, the pouch is a single-compartment pouch.

Thus, one variant consists in having a pouch that may be empty or that comprises beforehand:
 either at least one aqueous medium or at least the polymer or polymer salt to be crosslinked;
 or at least one aqueous medium comprising, already, said polymer or polymer salt to be crosslinked.

According to yet another particular embodiment, the pouch is a multi-compartment pouch, and more particularly a two-compartment pouch.

Thus, the pouch may have at least two compartments separated from one another by a membrane that is leaktight but is weak enough to tear under the action of a compression, each compartment being intended to store at least one compound used for the manufacture of a gel in accordance with the invention.

According to a first alternative, the first compartment comprises at least one aqueous medium, and the second compartment comprises at least one polymer or polymer salt.

According to a second alternative, the first compartment comprises at least one mixture of at least one aqueous medium in combination with at least one polymer or polymer salt, and the second compartment comprises at least one crosslinking agent.

According to a third particular embodiment, the pouch is a three-compartment pouch, each compartment possibly being dedicated respectively to packaging the polymer to be crosslinked, the aqueous medium and the crosslinking agent.

The latter two embodiments are not however favoured, regarding the lack of stability of certain crosslinking agents.

The embodiments described above make it possible to eliminate any step requiring contact of the gel with the outside environment, consequently significantly reducing the risks of contamination.

II) Process

A process according to the invention requires, firstly, having a cavity that comprises at least one aqueous medium with at least one polymer or polymer salts.

This relates more particularly to step a).

According to one alternative, the cavity according to the invention may contain only one of the two compounds, the second then being introduced subsequently thereinto.

In the embodiment where the receptacle is a two-compartment pouch in which the various compounds may advantageously be separated from one another within respective compartments, step a) then involves first breaking the membrane that separates these two compartments, for example by means of simple pressure.

1) Homogenization

According to the invention, the receptacle in question according to the invention allows an improved homogenization of the compounds used for the formation of a hydrogel in accordance with the invention.

The term "improved" is understood, within the meaning of the invention, to mean a homogenization quality greater than that observed with the conventional processes, but also a reduced homogenization time.

The objective of the homogenization is more particularly to completely dissolve the polymer in the aqueous medium and to arrange the formation of the chains of said polymer so as to activate the latter in readiness for the crosslinking.

The homogenization is considered to be satisfactory when the solution obtained has a homogenous coloration, without agglomerates, and a uniform viscosity.

As specified previously, the homogenization must be gentle enough to limit the degradation of the polymer chains.

This step is even more important when the polymer has a high molecular weight. This is because the hydration of such a compound then has a tendency to lead to the formation of a high-viscosity solution within which the appearance of lumps is commonly observed.

According to one particular embodiment, the deformable wall, or even the pouch has a degree of deformability such that the homogenization, considered in step b), may be carried out by optionally successive, mechanical deformations of the outer face of the deformable wall, or even of the pouch.

The deformations in question in the present application may be carried out using any means known to a person skilled in the art. The homogenization may be carried out manually, in particular by simple successive manual compressions of the outer faces of the wall or of said pouch, for example by palpations.

According to another alternative, the deformations may be carried out mechanically, for example using a device of "paddle mill" type, commonly used for the preparation of biological samples.

According to one such embodiment, the receptacle is placed in the device, then the homogenization is carried out by virtue of a system of two blades side-by-side which alternately press the deformable wall or at least one of the deformable walls following a back and forth motion.

According to another embodiment, the receptacle may be placed on a conveyor belt that exerts a back and forth motion, in the vicinity of which at least one roller is positioned, said roller being placed at a distance such that it exerts a compression on the deformable wall or at least one of the deformable walls during the passage thereof and thus generates a deformation of the latter conducive to the homogenization.

According to yet another embodiment, a pouch in accordance with the invention may be exposed to a back and forth motion between two diametrically opposed rollers, each of them exerting, during the passage of said pouch, a compression on each of the outer faces of the pouch.

A satisfactory homogenization time depends on the nature of the polymer, and more particularly on its molecular weight, on its concentration, on the operating conditions within the aqueous medium and also on the homogenization device used.

Homogenization times making it possible to obtain a sufficiently homogeneous hydrogel falls within the general knowledge of a person skilled in the art.

Preferably, the process according to the invention permits a homogenization time of less than 400 minutes, in particular of less than 150 minutes, even comprised between 30 and 100 minutes.

When the dissolution of the polymer or polymer mixture in the aqueous solvent is not completely satisfactory, as many agitation cycles as necessary are applied.

For example, the homogenization time necessary to obtain a satisfactory gel, starting from sodium hyaluronate of molecular weight greater than 0.5 MDa and a paddle mill, is around 40 to 120 minutes.

According to one particular embodiment, the homogenization may be carried out firstly by palpation, then using a mechanical device.

According to yet another embodiment, these various homogenization means may be used alternately.

2) Crosslinking

As mentioned previously, such a step requires particular conditions that depend simultaneously on the nature of the polymer, on its molecular weight, on the aqueous medium and on the nature of the crosslinking agent.

The term "conditions" is also understood to denote the element that initiates the crosslinking such as, for example, heating or UV exposure.

The choice of the initiation means suitable for obtaining a crosslinked gel falls within the general knowledge of a person skilled in the art.

Advantageously, the crosslinking step is carried out by thermal means.

In this regard, an initiation element of "heating" type may be achieved by:
   immersion of the receptacle, or even of the pouch, in a bath containing a hot fluid;
   exposure of the latter to radiation of certain wavelengths of UV type, for example, to microwave radiation or else to infrared irradiation.

In the case of crosslinking by thermal means, the receptacle in question according to the invention, and more particularly the pouch, makes it possible to keep one and the same temperature at any point of the gel that it contains. An optimized crosslinking in terms of homogeneity ensues therefrom.

The heating means and its intensity are of course adjusted with respect to the method of crosslinking, the degree of crosslinking and the viscosity of the gel that are desired.

A temperature particularly suitable for the step of crosslinking hyaluronic acid in the presence of a crosslinking agent such as BDDE is between 40 and 65° C.

However, other methods are also advantageously compatible with the receptacle in question according to the invention, such as:
   irradiation using ionizing radiation, like the process described in document US 2008/0139796;
   enzymatic crosslinking.

The degree of crosslinking also depends on the crosslinking time imposed on the gels. The longer the time is, the greater it will be, with however an optimum that should not be exceeded, at the risk of degrading the crosslinking agent and/or the polymer.

Thus, the crosslinking step may be carried out over a time ranging from 30 to 300 minutes, preferably from 100 to 200 minutes.

Advantageously, the crosslinking conditions are adjusted in order to obtain a degree of crosslinking such that the gel formed is a viscous, viscoelastic or even solid gel.

According to one particularly preferred embodiment, the step of crosslinking sodium hyaluronate is carried out in a basic medium, the pouch containing the corresponding gel being placed in a thermostatted bath brought to a temperature of around 50 to 55° C., for a period of 2 to 4 hours.

In order to homogeneously distribute the crosslinking agent within the viscous solution of hyaluronic acid, a homogenization step consecutive to the addition of said agent in the pouch may be envisaged. Such an operation may take place via palpations and/or mechanical agitation in the case of a pouch or by any other suitable means, over a period ranging from 15 to 20 minutes.

3) Stopping the Crosslinking

As is known previously, the stopping of the crosslinking (step f)) may take place prior to, together with or subsequent to the step e) of recovering the gel.

Such a step, according to a process in accordance with the invention, requires exposing the crosslinked gel or gel in the process of being crosslinked, or even the receptacle containing it, to conditions conducive the stopping of the crosslinking, or else to conditions capable of stopping the formation of bonds between the various polymer chains.

According to one preferred embodiment variant, step f) is carried out prior to step e). According to this advantageous embodiment, all of steps a) to f) are then carried out within said cavity, and the stopping of the crosslinking then consists in exposing the gel still present in the hermetic cavity to conditions conducive to this stopping of the crosslinking.

For example, with respect to the thermal conditions which will have been applied in order to initiate the crosslinking process, the crosslinking may be stopped:
   by simple withdrawal of the receptacle from the thermostatted bath, then by cooling until it returns to ambient temperature;
   by placing the receptacle in a bath of cold water, preferably at a temperature below ambient temperature, until the temperature inside said receptacle is close to ambient temperature; or
   by extracting the gel from said receptacle.

In the case of crosslinking via radiation, this is stopped via stopping the exposure of said gel to the radiation.

The crosslinked gel thus obtained may, for example, be demoulded from said receptacle, for example by simple opening of the receptacle or else by laceration of the deformable wall or one of its deformable wall(s).

The receptacle may also be provided with an opening system that makes it possible to extract, or even to demould, the crosslinked gel in its entirety without damaging its structure.

The crosslinked gel obtained at the end of the process as described previously is not generally directly injectable, due, in particular, to its excessively high polymer concentration and the possible presence of residues of crosslinking agents, or else to its physiological conditions or pH.

Figure 5:
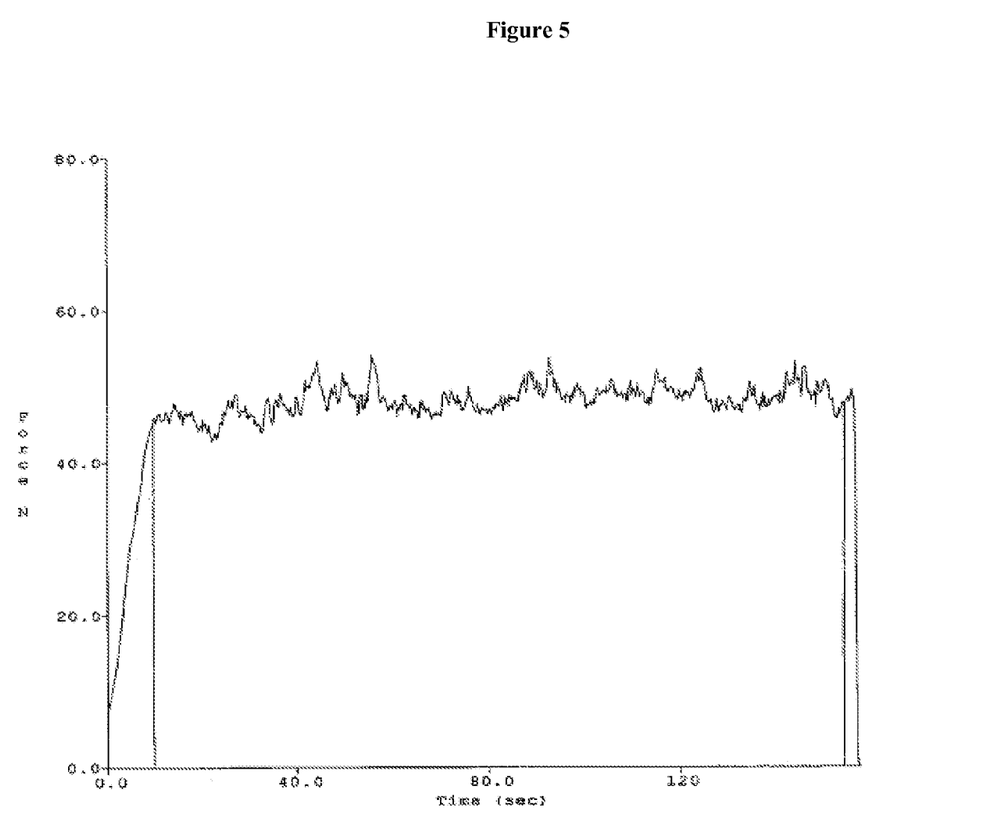
FIGS. 5 to 7: illustrate the injectability profile of samples 1, 2 and 3.
Figure 6:
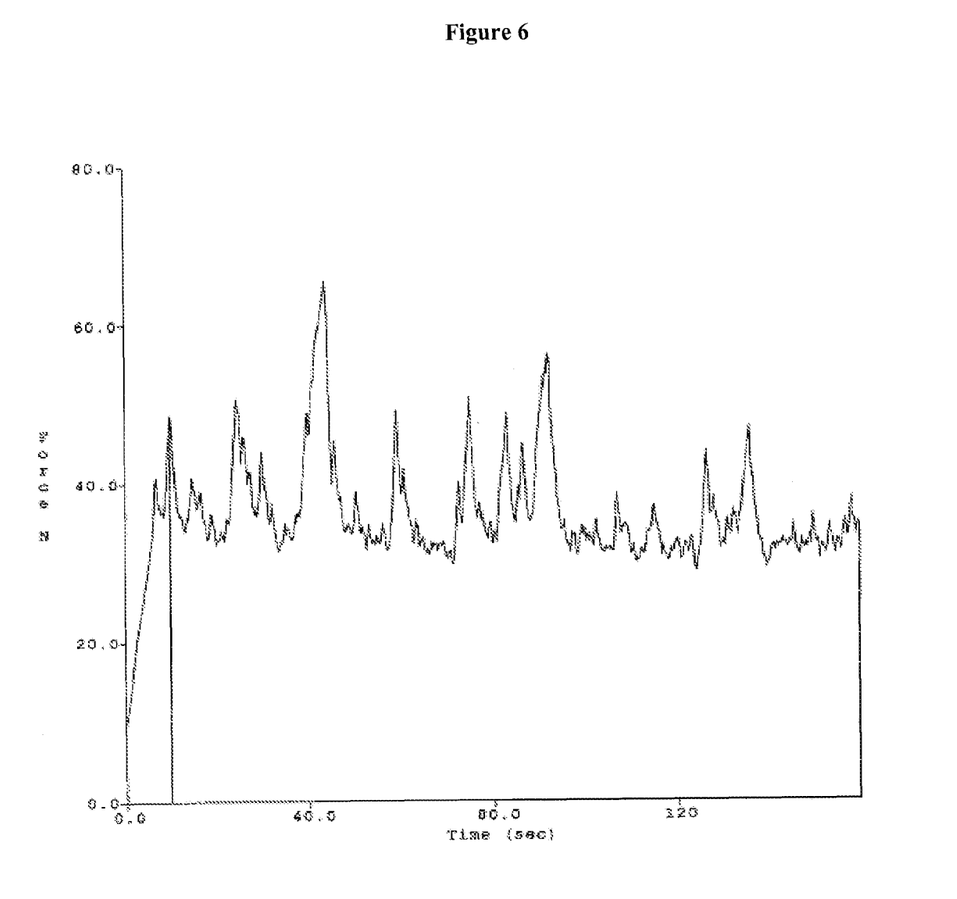
Figure 7:
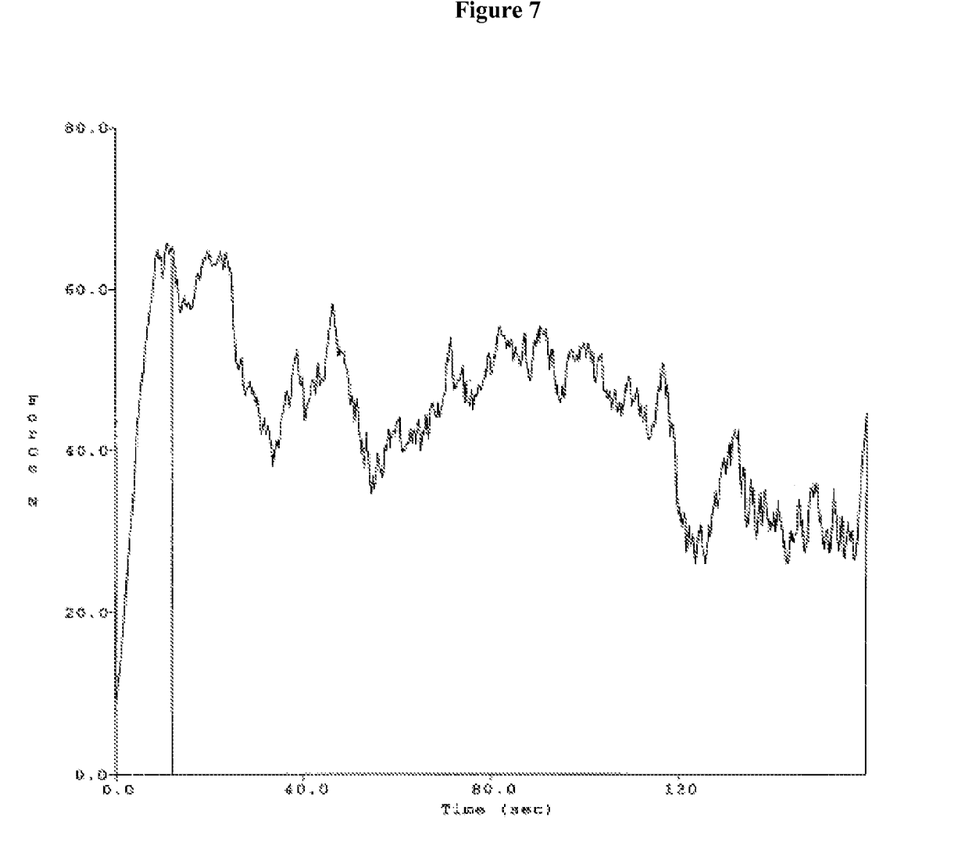

However, after a simple swelling in an aqueous medium, this gel obtained already has an injectability profile that is improved with respect to that which conventional gels have, as illustrated by FIGS. 5, 6 and 7.

The gel obtained at the end of the implementation of the process as described previously may especially have a stiffness that is too high in order to be injected into a patient as is.

Consequently, several additional steps, known to a person skilled in the art, are capable of being carried out.

More particularly, a step of neutralizing and expanding this gel is required in order to give it its implant qualities. The chains of the polymer network are then stretched and hydrated, whilst the pH is brought to that of the dermis.

A step of protection and of redensification of the gel is also capable of being carried out in order to further improve the qualities of the implant, according to the know-how of a person skilled in the art. The gel must be physiologically formulated by virtue of the presence of salts in equivalent amounts to those of the medium injected.

For a further improved purity, an additional purification step may be, in addition, carried out.

The last step consists in filling a syringe with the gel, which is carried out under controlled atmospheric conditions, followed by a final heat sterilization which takes place immediately after the syringe filling.

III) Polymer

The term "polymer" in accordance with the invention is understood to mean any macromolecule constituted of the repeated linkage of one and the same unit or of different units, connected to one another by covalent bonds.

A polymer is more particularly selected with respect to the properties that it is desired to see the crosslinked gel obtained according to the invention display. More particularly, such a polymer must have a good biocompatibility.

Thus, a physiologically acceptable polymer or polymer salt may be of natural or synthetic origin.

The polymers suitable for the invention may especially be chosen from glycosaminoglycans such as chondroitin sulphate, keratan, keratan sulphate, heparin, heparin sulphate, xanthan, carrageenan, polysaccharides such as hyaluronic acid, chitosan, cellulose and derivatives thereof, alginate, starch, dextran, pullulan, galactomannan and biologically acceptable salts thereof, a protein or a synthetic polymer such as polyacrylic acid or polyvinyl alcohol, and preferably among polysaccharides.

The polysaccharide salts in accordance with the invention are more particularly chosen from the physiologically acceptable salts, such as the sodium salt, the potassium salt and the mixture thereof, preferably the sodium salt.

One particularly preferred polysaccharide is hyaluronic acid or one of its salts, preferably sodium hyaluronate (NaHA).

As precited, the process of the invention advantageously allows the implementation of polymers having a very high molecular weight, and especially polymers having a molecular weight greater than 4 MDa, unlike the conventional methods of homogenization.

Preferably, a polymer or polymer salt according to the invention has a high molecular weight, preferably a molecular weight greater than or equal to 100 000 Da, or even greater than 3 MDa depending on the application in question.

This polymer is formulated in step a) of the process according to the invention in an aqueous medium.

The expression "aqueous medium" in accordance with the invention is understood to mean any liquid medium which has the property of dissolving a polymer, and more specifically, a polysaccharide or one of its salts.

The nature of the aqueous medium is more particularly conditioned with respect to the type of crosslinking envisaged but also with respect to the type of polymer used.

In this regard, an aqueous medium capable of being suitable may be either acid, or basic.

One particularly preferred aqueous medium is an alkaline medium, preferably sodium hydroxide (NaOH), more particularly a solution of sodium hydroxide having a pH greater than 12.

IV) Crosslinking Agent

The expression "crosslinking agent" in accordance with the invention is understood to mean any compound capable of inducing a crosslinking between the various polymer chains.

The choice of this crosslinking agent with respect to the polymer to be crosslinked clearly falls within the competence of a person skilled in the art.

A crosslinking agent in accordance with the invention is chosen from epoxides, aldehydes, polyaziridyl compounds, divinyl sulphone (DVS) or butanediol diglycidyl ether (BDDE), preferably butanediol diglycidyl ether, the latter having the lowest toxicity among the standard crosslinking agents.

The crosslinking agent, of changeable and very often unstable nature, is, within a receptacle in accordance with the invention, stored in a protective environment thus guaranteeing that the subsequent crosslinking step takes place successfully.

The process according to the invention also guarantees a rapid, complete and uniform diffusion of the crosslinking agent through the network of polymer chains.

A substantial improvement in the quality and in the yield of the crosslinking ensues therefrom, and also a sizeable reduction in the amount of crosslinking agent required compared to conventional processes.

The adjustment of the amount of crosslinking agent for carrying out the crosslinking reaction also clearly falls within the competence of a person skilled in the art.

According to one particularly preferred embodiment, the process according to the invention implements sodium hyaluronate in an alkaline medium with butanediol diglycidyl ether (BDDE), as crosslinking agent.

The following examples and figures are presented by way of illustration of the invention in a non-limiting manner.

BRIEF DESCRIPTION OF THE DRAWINGS

Figures

EXAMPLES

The comparative studies below are carried out on three samples of crosslinked hyaluronic acid gels illustrating either a process in accordance with the invention (sample 1), or a conventional process (samples 2 and 3).

Sample 1: process carried out in a 400 ml sterile pouch, agitation with a paddle mill, crosslinking for 3 hours at 52° C., Sample 2: process carried out in a 400 ml sterile plastic pot, agitation with a spatula; crosslinking for 3 hours at 52° C., Sample 3: process carried out in a 400 ml sterile plastic pot, agitation with a spatula; crosslinking for 3 hours at 55.5° C.

Example 1

Preparation of the Homogeneous Hyaluronic Acid Gel

For each of the samples, 10 g of NaHA are dissolved in a 1% sodium hydroxide solution so as to obtain a solution containing 12% of NaHA.

The pouch (working volume: 400 ml, length: 310 mm, width: 180 mm, food grade PE) in which sample 1 is dissolved is exposed to a mechanical homogenization. In order to do this, the pouch is exposed to successive agitation cycles for a total duration of 1 hour at 210 rpm (22 rad·s$^{-1}$) using a paddle mill.

For samples 2 and 3, the agitation is manual via a sterile stainless steel spatula for 5 to 10 minutes, followed by a new manual agitation cycle every 30 minutes up to complete hydration.

The dissolution of the NaHA is considered complete once all of the NaHA is hydrated and the solution is perfectly homogeneous (absence of agglomerates and uniform colour). In the case where the dissolution does not appear to be complete, a supplementary agitation cycle may be carried out.

The total dissolution times of the NaHA in the 1% sodium hydroxide solution for the three samples are indicated in Table 1 below.

TABLE 1

Total dissolution time

| | Sample 1 (pouch) | Sample 2 (pot) | Sample 3 (pot) |
|---|---|---|---|
| Total dissolution time (minutes) | 60 | 114 | 106 |

The homogenization of the hyaluronic acid in the pouch is faster than the homogenization in a pot with a spatula without requiring an increase in temperature, like with sample 3. This alternative is also cleaner since the gel is not in contact with the outside and there is no direct friction on the reaction medium which could generate particles.

Example 2

Crosslinking

A solution of BDDE diluted to $\frac{1}{5}^{th}$ in a 1% sodium hydroxide solution is added, for each of the samples obtained in Example 1, to the homogeneous NaHA solution obtained at the end of the preceding step.

The homogenization of the reaction medium of sample 1 is then carried out by virtue of successive agitation cycles each comprising:

5 to 10 minutes of manual agitation via kneading of the pouch; and 5 of agitation using a paddle mill at 210 rpm (22 rad·s$^{-1}$).

The homogenization of the reaction media of the samples 2 and 3 is carried out by agitation with a sterile stainless steel spatula for 15 minutes.

Three temperature probes are then placed in each of the products to be crosslinked (two at the periphery and diametrically opposed, and one in the middle) in order to be able to record the temperatures within the reaction medium during the crosslinking reaction.

For sample 1, the sealed pouch is placed in a water bath at 52° C. for 3 hours, making sure that the opening of the pouch remains outside of the bath.

For the samples 2 and 3, the pots are placed in the water bath for 3 hours, respectively at 52° C. and at 55.5° C.

The temperature within the reaction medium was monitored throughout the crosslinking reaction by virtue of three temperature probes.

Figure 2:
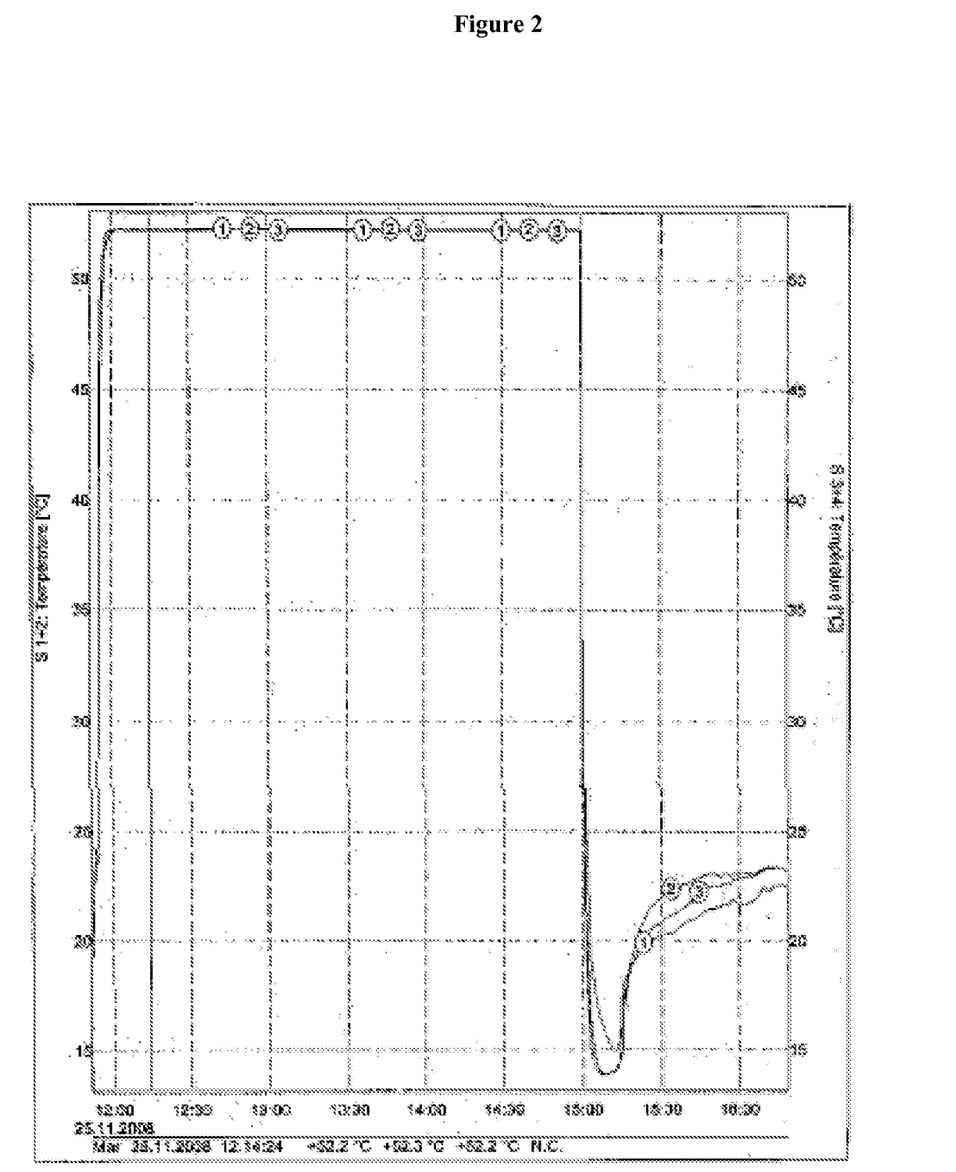
FIGS. 2, 3 and 4: respectively illustrate the change in the temperature during the crosslinking reaction of samples 1, 2 and 3.
Figure 3:
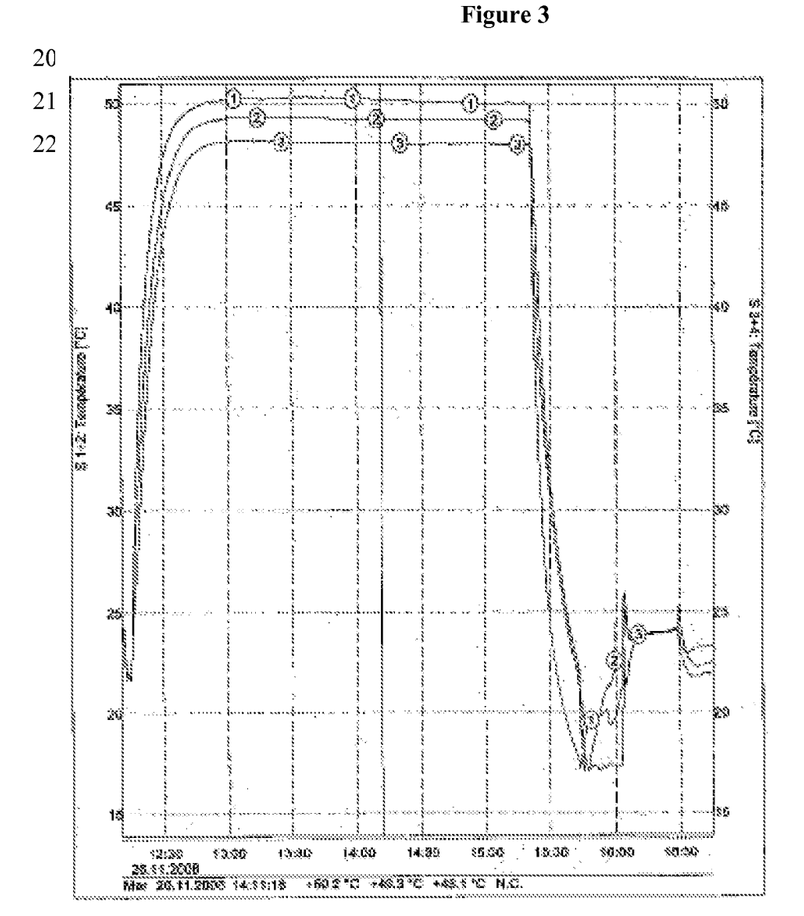
Figure 4:
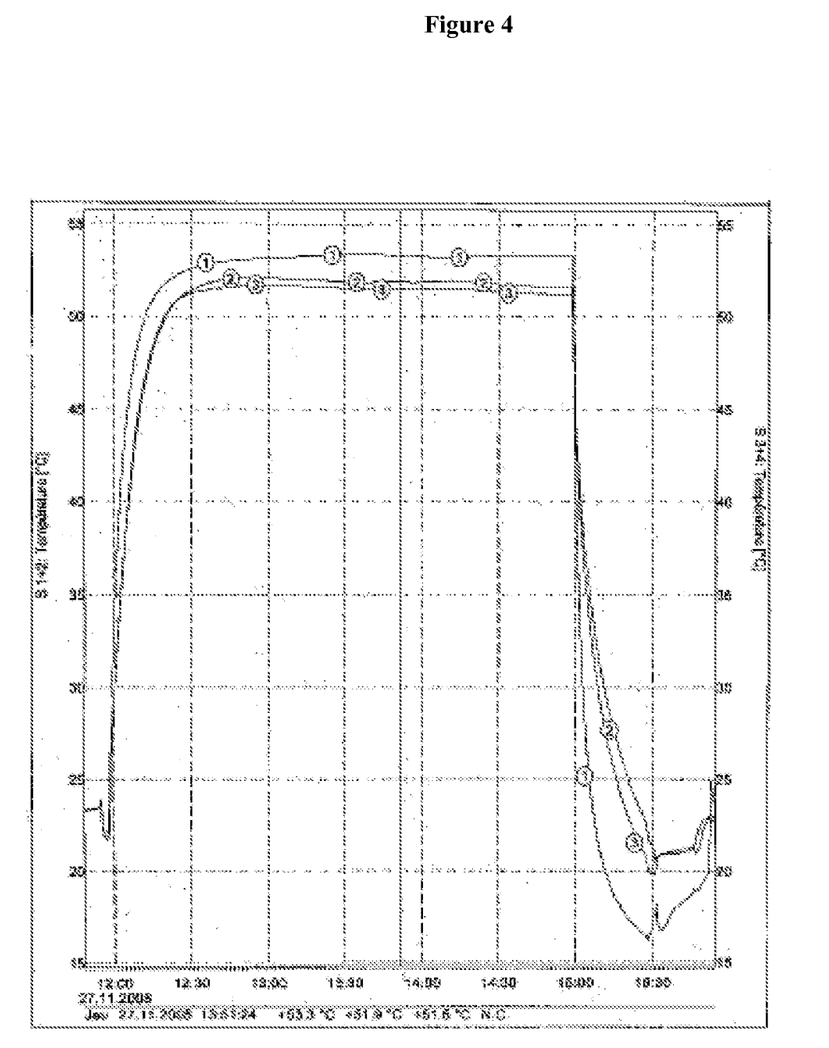

FIGS. 1 to 3 represent the temperature profiles observed during the crosslinking reactions of the three samples.

The numbers 1 to 3 on each profile correspond to the three temperature probes which were placed in the pouch or in the pots in order to monitor the change in temperature within the reaction medium.

For sample 1, an almost immediate rise in temperature within the pouch, then a uniform hold of the temperature of the reaction medium at around 52° C. is observed irrespective of the temperature probe. The temperature is therefore uniform throughout the reaction medium.

For the samples 2 and 3, a slower rise in temperature than for the pouch process is, on the other hand, observed then marked differences are observed between the temperatures measured by the three different probes around 52° C. (sample 2) or 55.5° C. (sample 3). The temperature is therefore not uniform throughout the reaction medium.

Once the crosslinking reaction is finished, the pouch and the pots are withdrawn from the thermostatted bath and placed in a container that contains refrigerated sterile water until the temperature has cooled to 25° C. (ambient temperature).

The yield is defined by relating the weight of the product obtained to the weight of starting reactants.

TABLE 2

Weight yields of the crosslinking reactions

| | Sample 1 (pouch) | Sample 2 (pot) | Sample 3 (pot) |
|---|---|---|---|
| Yield (%) | 99.6 | 94.5 | 94.6 |

It is observed that the yield of the crosslinking reaction carried out in a pouch is better than that of the reaction carried out in a pot, even in the presence of a temperature increase.

Example 3

Characterization of the Gels Obtained in Example 2

1) Protocol

The three samples of crosslinked gels obtained in Example 2 are divided into small cubes of around 1 cm$^3$.

For each gel obtained, the pieces are introduced into a sterile 1 L rigid plastic pot containing the appropriate amount of pyrogen-free sterile phosphate buffer (PB) to bring the gel to a concentration of 20 mg/g. The amount of PB solution is adjusted so as to obtain a gel containing 20 mg/m of HA. The amount of hydrochloric acid is adjusted so as to neutralize the pH. The content of the pot is agitated for 5 minutes using a sterile stainless steel spatula. The pot is then placed in a three-dimensional agitator for 20 hours at ambient temperature.

The crosslinked gels thus obtained have a pH close to neutrality and a physiological concentration of NaCl.

For each sample obtained according to this step, a given amount of product is withdrawn using five 1 ml BD Hypack® glass syringes in order to carry out measurements of the injectability forces (27G1/2 hypodermic needle) and of the pH.

The measurements of the pH and of the injectability forces are presented in the table below (Table 3). The syringes filled with crosslinked gel were subjected to a compression of 12.5 N·mm$^{-1}$ and the values of the measurement of injectability forces obtained represent an average of the measurements carried out on three syringes for each crosslinked gel.

TABLE 3

| Measurements of the pH and of the injectability forces | | | |
|---|---|---|---|
| | Sample 1 (pouch) | Sample 2 (pot) | Sample 3 (pot) |
| pH | 7.3 | 7.2 | 6.9 |
| Injectability force (N) | 45.6 | 34.7 | 43 |
| Standard deviation (%) | 5.6 | 5.2 | 16.7 |

It was also observed by the inventors that the gels resulting from the pouch process have a greater tolerance for sterilization, in terms of rheological properties, than the gels obtained by the pot process.

Moreover, it is observed that the process used for the implementation of sample 1 makes it possible to obtain a crosslinked gel for which the residual content of BDDE before crosslinking is substantially lower than that recorded for samples 2 and 3, by around a factor of 2.

What is claimed is:

1. A process for preparing a crosslinked gel of hyaluronic acid or one of its salts, comprising at least the steps of:
   a) providing an aqueous medium containing said hyaluronic acid or one of its salts;
   b) forming a homogeneous gel from the medium from step a), wherein the homogenization takes place over a duration ranging from 30 to less than 150 minutes;
   c) bringing the gel obtained in step b) into contact with an effective amount of butanediol diglyceryl ether, forming a mixture;
   d) crosslinking said mixture formed in step c), forming a crosslinked hydrogel; and
   e) recovering said the crosslinked hydrogel;
      wherein at least said steps a) to d) are carried out within a hermetic deformable pouch.

2. The process according to claim 1, further comprising a step f) of stopping the crosslinking, said step f) being carried out prior to, together with or subsequent to the recovery step e).

3. The process according to claim 2, wherein the crosslinking step f) is carried out prior to the recovery step e).

4. The process according to claim 3, wherein all of steps a) to d) and f) are carried out within said deformable pouch.

5. The process according to claim 1, wherein said deformable pouch has a degree of deformability such that it can be deformed manually by palpation.

6. The process according to claim 1, wherein said deformable pouch is equipped with an opening system.

7. The process according to claim 1, wherein said deformable pouch is made of plastic.

8. The process according to claim 1, wherein said deformable pouch is a single-compartment pouch.

9. The process according to claim 1, wherein the homogenization is carried out by deformations in said deformable pouch.

10. The process according to claim 9, wherein the deformations are carried out manually.

11. The process according to claim 9, wherein the deformations are carried out mechanically.

12. The process according to claim 1, wherein the crosslinking takes place over a duration ranging from 30 to 300 minutes.

13. The process according to claim 1, wherein the recovery of the crosslinked gel is carried out by demolding said gel.

14. The process according to claim 1, wherein the crosslinked gel is a solid gel.

15. The process according to claim 1, wherein the crosslinked gel is a biomaterial.

16. The process according to claim 1, wherein the hyaluronic acid or one of its salts is sodium hyaluronate.

17. The process according to claim 1, further comprising crosslinking said mixture at a temperature of between 40° C. and 65° C.

* * * * *